United States Patent [19]

DeCrosta et al.

[11] Patent Number: 4,666,705

[45] Date of Patent: May 19, 1987

[54] CONTROLLED RELEASE FORMULATION

[75] Inventors: Mark T. DeCrosta, Plainsboro; Nemichand B. Jain, Monmouth Junction; Edward M. Rudnic, Kendall Park, all of N.J.

[73] Assignee: E. R. Squibb & Sons, Inc., Princeton, N.J.

[21] Appl. No.: 740,672

[22] Filed: Jun. 3, 1985

[51] Int. Cl.$^4$ .......................... A61K 9/22; A61K 9/26
[52] U.S. Cl. ...................... 424/482; 424/81; 424/470
[58] Field of Search ............... 424/19, 22, 81

[56] References Cited

U.S. PATENT DOCUMENTS

| | | | |
|---|---|---|---|
| 2,987,445 | 6/1961 | Levesque | 424/22 |
| 3,065,143 | 4/1960 | Christenson et al. | 167/82 |
| 3,074,852 | 1/1963 | Mayron | 424/81 |
| 3,330,729 | 7/1967 | Johnson | 424/81 |
| 3,362,881 | 1/1968 | Eberhardt | 424/22 |
| 3,427,378 | 2/1969 | Henderson et al. | 424/14 |
| 3,444,290 | 5/1969 | Wal et al. | 424/4 |
| 3,458,622 | 3/1969 | Hill | 424/19 |
| 3,555,151 | 1/1971 | Kaplan et al. | 424/156 |
| 3,574,820 | 4/1971 | Johnson et al. | 424/22 |
| 3,594,467 | 7/1971 | Christenson et al. | 424/22 |
| 3,634,584 | 1/1972 | Poole | 424/22 |
| 3,976,764 | 8/1976 | Watanabe et al. | 424/19 |
| 4,059,686 | 11/1977 | Tanaka et al. | 424/81 |
| 4,140,755 | 2/1979 | Sheth | 424/21 |
| 4,173,626 | 11/1979 | Dempski et al. | 424/19 |
| 4,248,857 | 2/1981 | DeNeale et al. | 424/21 |
| 4,250,163 | 2/1981 | Nagai et al. | 424/81 |
| 4,252,786 | 2/1981 | Weiss et al. | 424/19 |
| 4,259,314 | 3/1981 | Lowey | 424/19 |
| 4,309,404 | 1/1982 | DeNeale et al. | 424/21 |
| 4,309,405 | 1/1982 | Guley | 424/21 |
| 4,389,393 | 6/1983 | Schor et al. | 424/19 |
| 4,461,759 | 7/1984 | Dunn | 424/22 |
| 4,499,066 | 2/1985 | Moro et al. | 424/22 |
| 4,547,359 | 10/1985 | Zierenberg | 424/81 |

*Primary Examiner*—Shep K. Rose
*Attorney, Agent, or Firm*—Lawrence S. Levinson; Burton Rodney

[57] ABSTRACT

A controlled release pharmaceutical formulation which undergoes slow release of active drug is provided, preferably in the form of a tablet containing medicament, such as captopril, is slowly released over a controlled length of time. The tablet also includes an acrylic acid polymer or copolymer and one or more lubricants and is formed by a dry granulation technique.

16 Claims, No Drawings

CONTROLLED RELEASE FORMULATION

FIELD OF THE INVENTION

The present invention relates to a controlled release formulation, preferably in the form of a tablet, for slowly releasing medicament, such as the angiotensin-converting enzyme inhibitor captopril.

BACKGROUND OF THE INVENTION

It is of great advantage to both the patient and clinician that medication be formulated so that it may be administered in a minimum number of daily doses from which the drug is uniformly released over a desired extended period of time. Until now, this has been accomplished in several different ways. Medicinal agents are either coated with varying thicknesses of a relatively insoluble material or are embedded into a rigid lattice of resinous material. The medicinal agent is continuously made available for absorption into the blood stream to replace the amount eliminated while the dosage form is passing through the gastro-intestinal tract of the patient. However, certain types of medicinal agents are not suited to absorption during passage through the gastro-intestinal tract. For example, most acidic medicinals are principally absorbed from the stomach, whereas most basic medicinals are absorbed primarily from the intestines.

U.S. Pat. No. 3,458,622 to Hill discloses a controlled release tablet for the administration of medicinal agents over a prolonged period of up to about eight hours. This patent discloses a compressed tablet for the prolonged release of a medicament containing that medicament in a core formed from a polymeric vinyl pyrrolidone, preferably polyvinyl pyrrolidone (PVP), and a carboxyvinyl hydrophilic polymer (hydrocolloid) such as those marketed under the trademark Carbopol wherein the combined weight of the two polymeric materials may exceed half the weight of medicament but should be kept below about 75% of the weight of medicament. The tablet is formed employing a wet granulation technique. The core material formed from the two polymeric substances provides the controlled release effect by forming a complex of lower water-solubility under the action of water or gastric fluid, without swelling of the polymeric substances. This complex is gum-like in consistency and retards the diffusion of active ingredient from the tablet. The controlled release rate of the drug is dependent upon the interaction of the two principal ingredients, the polymer and the hydrocolloid, in the presence of water to form a gummy complex of low solubility. Since little of the gummy complex is present initially, the drug at or near the surface dissolves fairly rapidly and there is an initial surge wherein a relatively large amount of drug is released in the beginning for a period of about one hour. As the colloid complex is formed, once aqueous solution penetrates the surface of the tablet, the gel retards the dissolution of the drug out of the tablet.

DE No. 3314003-A dated Apr. 4, 1983 (Boehringer Ingelheim) is similar in disclosure U.S. Pat. No. 3,458,622 to Hill and discloses divisible, delayed release tablets containing a molecular dispersion of active ingredient in a polyacrylate carrier together with lactose, polyvinylpyrrolidone, starch, colloidal silicic acid and magnesium stearate, which are prepared by wet granulation.

U.S. Pat. No. 4,252,786 to Weiss et al recognizes the initial surge problem in the Hill patent and resolves same by applying a rupturable relatively water-insoluble water-permeable film formed of a combination of hydrophobic and hydrophilic polymers over an insoluble swelling type delayed release matrix or core containing the medicament which core includes a blend of polyvinyl pyrrolidone and a carboxyvinyl hydrophilic polymer. Weiss et al in Column 2 states as follows:

"Initially, while the film is intact, the release of the drug contained in the matrix is primarily controlled by diffusion of solvent and solute molecules through the film. As water or gastric fluid permeates through the film, the gummy complex forms and the slight swelling of the complex causes the film to rupture or erode. The release rate is then controlled by the gummy complex. The application of a relatively water insoluble, water permeable film primarily controls the drug release rate while the matrix gel is being generated and a smoother, gradual, more uniform release rate is achieved during the entire period of about eight to twelve hours, approaching a zero order release pattern. The release pattern of the core, upon application of the film, can be varied over a range by varying the composition and amount of film-forming mixture."

U.S. Pat. No. 4,140,755 to Sheth et al discloses a sustained release formulation in the form of sustained release tablets which are hydrodynamically balanced to have a bulk density (specific gravity) of less than 1 in contact with gastric fluid and which will therefore remain floating in gastric fluid which has a specific gravity of between 1.004 and 1.010. The Sheth et al sustained release formulation contains a homogeneous mixture of one or more medicaments with one or more hydrophilic hydrocolloids, such as hydroxypropyl methyl cellulose having a viscosity of 4000 cps. The hydrocolloids when contacted with gastric fluid at body temperatures form a sustained gelatinous mix on the surface of the tablet causing the tablet to enlarge and acquire a bulk density of less than 1. The medicament is slowly released from the surface of the gelatinous mix which remains buoyant in the gastric fluid.

All of the medicament in the tablet disclosed in the Sheth et al patent is released in the stomach.

U.S. Pat. Nos. 4,309,404 and 4,248,857 to DeNeale et al disclose slow release formulations for many different drugs and classes of drugs including propranolol and other antihypertensives which formulations are formed of a core material containing the active drug (31–53%), carboxypolymethylene (7–14.5%), zinc oxide (0–3%), stearic acid (4.5 to 10%) and mannitol (3 to 30%); a seal coating surrounding the core; and a sugar coating surrounding the seal coating.

U.S. Pat. No. 4,309,405 to Guley et al discloses a sustained release tablet similar to that disclosed in DeNeale et al (U.S. Pat. No. 4,309,404) except that the core contains 20 to 70% drug, 30 to 72% of a mixture of a water-soluble polymer such as hydroxypropylmethyl cellulose or hydroxypropyl cellulose and water-insoluble polymer (ethylcellulose alone or in admixture with carboxypolymethylene, hydroxypropyl cellulose and the like).

Each of the DeNeale et al and Guley et al patents disclose that their compositions provide substantially zero order release of the core contained drug for about 12 hours following the first hour of administration. Thus, zero order release is only obtained after the initial surge of release of drug in the first hour.

U.S. Pat. No. 4,259,314 to Lowey discloses a controlled long-acting dry pharmaceutical composition which includes a dry carrier formed from a mixture of hydroxypropylmethyl cellulose (viscosity of 50 to 4000 cp in 2% aqueous solution at 20° C.) and hydroxypropyl cellulose (viscosity of 4000 to 6500 cp for a 2% aqueous solution at 25° C.) which dry carrier is employed with a therapeutic agent among which include aspirin, ascorbic acid and nitroglycerin.

U.S. Pat. Nos. 3,065,143 to Christenson et al, 3,147,137 to Playfair, 3,444,290 to Wal et al, 3,427,378 to Henderson et al, 3,555,151 to Kaplan et al, 3,574,820 to Johnson et al, and 3,976,764 to Watanabe and 4,173,626 to Dempski et al disclose various sustained release tablets which include gelling agents none of which includes as the active ingredient an angiotensin converting enzyme inhibitor.

U.S. Pat. No. 4,389,393 to Schor et al discloses a carrier base material to be combined with a therapeutically active medicament into a solid dosage form. The carrier base material is one or more hydroxypropylmethyl celluloses, or a mixture of one or more hydroxypropylmethyl celluloses and up to 30% by weight of the mixture of methyl cellulose, sodium carboxymethyl cellulose and/or other cellulose ether, wherein at least one of the hydroxypropylmethyl celluloses has an average molecular weight of at least 50,000, the carrier base material constituting less than one-third of the weight of the solid unit dosage form.

U.S. Pat. No. 4,434,153 to Urquhart discloses a drug delivery system formed of a swellable hydrogel reservoir or matrix such as an acrylic acid polymer matrix containing tiny pills formed of a wall surrounding a drug core.

DESCRIPTION OF THE INVENTION

In accordance with the present invention, a controlled release formulation for the time release of medicament, preferably in the form of a tablet, is provided, which is exceptional in that it is capable of high drug loading and as a release mechanism for controlled release of medicaments, such as captopril, over a period of 4 to 16 hours. The controlled release formulation of the invention is in the form of a tablet formed by a dry granulation technique, which includes medicament, one or more water-soluble or water-swellable acrylic acid polymer or copolymer hydrocolloid gelling agents and one or more lubricants. The tablet of the invention neither includes nor requires a coating.

Upon oral ingestion of the sustained release tablet of the invention, the tablet contacts the gastric fluid and very slowly erodes; the acrylic acid polymer or copolymer particles hydrate and swell to form a gelatinous mass which acts as a protective barrier. Medicament is released by diffusion or leaching through the gel layer. In fact, the medicament is released in a controlled manner for a period of up to 16 hours or more to provide substantially the same therapeutic efficacy for the drug as provided by the identical dosage of drug administered in divided doses.

It has been found that controlled release of the medicament from the tablet is possible even without the presence of a coating.

The controlled release tablet of the invention will include medicament in an amount within the range of from about 20 to about 65% by weight, preferably in an amount within the range of from more than 25 to about 35% by weight of the tablet. The acrylic acid polymer or copolymer will be present in an amount within the range of from about 50 to about 80%, and preferably from about 55 to about 75% by weight of the tablet; and the lubricant will be present in an amount within the range of from about 0.5 to about 8%, and preferably from about 1 to about 4% by weight of the tablet. Thus, the acrylic acid polymer or copolymer will be present in the tablet of the invention in an amount of at least about 1 and preferably about 2 or more times the amount of medicament present.

A wide variety of medicaments which are orally administered in tablet form can be used in the form of tablets prepared according to this invention. These include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyridamine and the like, hypotensive agents such as rauwolfia, reserpine and the like, cardioactive agents such as bendroflumethiazide, flumethiazide, chlorothiazide, aminotrate, propranolol, nadolol, metoprolol, atenolol, procainamide and the like, angiotensin converting enzyme inhibitors such as captopril and enalapril, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, erythromycin, streptomycin, cephradine and other cephalosporins, penicillin, semisynthetic penicillins, griseofulvin and the like, sedatives such as chloral hydrate, phenobarbital and other barbiturates, glutethimide, antitubercular agents such as isoniazid and the like, analgesics such as aspirin, acetominophen, propoxyphene, meperidine, ibuprofen, and the like, etc. These substances are frequently employed either as the free compound or in a salt form, e.g., acid addition salts, basic salts like alkali metal salts, etc. Other therapeutic agents having the same or different physiological activity can also be employed in pharmaceutical preparations within the scope of the present invention.

The invention is particularly adapted for controlled release tablets containing the angiotensin-converting enzyme inhibitor captopril. In fact, it has been found that the bioavailability of captopril in the tablets of the invention is at least 50% greater than previously possible.

The controlled release formulation of the invention may optionally include an auxilliary hydrocolloid gelling agent which absorbs water, swells and forms a gel. It will be of the type to provide a viscosity of 10,000 to 200,000 centipoises in a 2% aqueous solution at 20° C., will have a molecular weight ranging from about 80,000 to about 300,000, and will be present in an amount small enough to ensure that a controlled release is obtained. The auxiliary hydrocolloid is provided in an amount within the range of from about 30 to about 80% by weight and preferably from about 50 to about 70%.

Examples of auxiliary hydrocolloids which may be employed herein have a viscosity of more than 10,000 centipoises as indicated above, and will preferably comprise cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million). Preferred are sodium carboxymethyl cellulose, methyl cellulose, hydroxypropylmethyl cellulose and carboxypolymethylene. However, it is to be understood that any hydrocolloid may optionally be employed in the present invention, such as, for example, gum acacia, guar gum, gum tragacanth, gum xanthan, an alkali metal or alkaline earth metal carageenate, alginates, such as alginic acid, ammonium or sodium alginate or mixtures thereof.

Other examples of suitable hydrocolloids are set out in U.S. Pat. No. 4,140,755 to Sheth et al.

The acrylic acid polymer or copolymer employed in the controlled release tablet of the invention will preferably be a carboxyvinyl hydrophilic polymer of acrylic acid crossed-linked with a polyfunctional agent such as a polyalkenyl ether, for example, polyalkyl sucrose, and will have the general formula

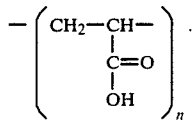

Examples are carboxypolymethylene (Carbopol 934 or Carbopol 934P, pharmaceutical grade having a molecular weight of about 3,000,000, products of B. F. Goodrich) or other polymers described in U.S. Pat. No. 2,909,462, a cross-linked copolymer of acrylic acid and a hydrophobic polymer also referred to as Carbopol 101 (product of B. F. Goodrich), poly(hydroxyalkylmethacrylates), polyacrylamides such as sold under the trademark Cyanamer ®, polyacrylic acid, polyethylene oxide, starch graft copolymers sold under the trademark Good-rite ®, Aqua-Keeps ® acrylate polymer, polyvinyl ether maleic anhydride hydrolyzed with a solution of sodium and calcium ions, also known as Gantrez MS455, ester cross-linked polyglucan, copolymers of methyl and/or ethyl esters of acrylic acid and methacrylic acid, for example, with a mean molecular weight ranging from 500,000 to 1,000,000. Preferred are the acrylic acid polymers or copolymers referred to by the trademark Carbopol 934 and Carbopol 101.

Lubricants which may be employed herein include those of the water-insoluble type such as magnesium stearate, calcium stearate, sodium stearate, stearic acid, sterotex, talc, waxes, and/or hydrogenated vegetable oils and carnauba wax, and those of the water-soluble type, such as boric acid, sodium benzoate, sodium acetate, sodium chloride, DL-leucine, Carbowax 4000, Carbowax 6000, sodium oleate, sodium lauryl sulfate and/or magnesium lauryl sulfate.

Preferred are magnesium stearate and/or stearic acid.

The tablet of the invention may also optionally include one or more non-swellable binders which bind the other ingredients of the tablet to prevent premature disintegration and promote proper release rate. The binders will be present in an amount within the range of from 0 to about 8% and preferably from about 2 to about 5% by weight of the tablet. Examples of such binders suitable for use herein include, but are not limited to, lactose, gelatin, starches such as corn starch, modified corn starch, sugars, gum acacia and the like.

In addition to, or in lieu of, the above-described non-swellable binders, the tablet of the invention may optionally contain a wax binder in finely powdered form of average particle size of, for example, less than 500 microns and preferably within the range of from about 150 to about 500 microns, in an amount within the range of from 0 to about 8% and preferably from about 2 to about 5% by weight of the tablet. Examples of such wax binders suitable for use herein include, but are not carnauba wax, paraffin, spermaceti, polyethylenes or microcrystalline wax.

It will be appreciated that at least one of the non-swellable binders, and/or one of the wax binders, preferably carnauba wax, may be present where neither the medicament nor the acrylic acid polymer or copolymer and/or auxiliary hydrocolloid gelling agent is compressible and such binder together with the acrylic acid polymer or copolymer and/or auxiliary hydrocolloid will form a water-insoluble matrix.

The sustained release tablets will optionally include additional edible non-toxic ingredients as conventionally employed in solid medicinal dosage forms. Thus, the tablets of the invention may optionally include one or more excipients in an amount within the range of from about 1% to about 25% by weight and preferably from about 1% to about 10% weight such as lactose, sugar, corn starch, modified corn starch, mannitol, sorbitol, inorganic salts such as calcium carbonate. Other conventional ingredients which may optionally be present include preservatives, stabilizers, anti-adherents or silica flow conditioners or glidants, such as Syloid brand silicon dioxide as well as FD&C colors.

The combined weight of the components of the tablet (with the exclusion of the medicament) is at least about 100% and preferably about 200% or more of the weight of the medicament or active drug ingredient present. Finished tablets having a total weight of up to 1 gm or even more can be prepared.

A preferred sustained release tablet in accordance with the present invention will inlucde from about 20 to about 40% by weight captopril, from about 50 to about 80% by weight of the acrylic acid polymer or copolymer which preferably is polyacrylic acid cross-linked with polyallyl sucrose (Carbopol 934 or 934P, B. F. Goodrich) and from about 1 to about 4% by weight of one or more tabletting lubricants which preferably is a mixture of magnesium stearate and stearic acid (all of such % being based on the weight of the tablet), and optionally from 0 to about 5% by weight of a flow aid agent which preferably is a silica flow agent.

The sustained release tablets of the invention may be prepared as follows. The medicament, in powdered form, acrylic acid polymer or copolymer, tabletting lubricant and other optional ingredients are mixed in a suitable blender and then compressed into the tablets of the invention. Wet granulation techniques are not employed.

The following Examples represent preferred embodiments of the present invention.

EXAMPLE 1

A sustained release formulation capable of slowly releasing the angiotensin-converting enzyme captopril for a period of up to 16 hours or more and having the following composition was prepared as described below.

| Ingredient | Amount per batch (g) | Per Dosage Unit (mg) |
|---|---|---|
| Captopril | 325 | 100 |
| Acrylic acid polymer cross-linked with polyallyl sucrose (Carbopol 934P) | 650 | 200 |
| Stearic acid | 19.5 | 6 |

The above ingredients, in powder form, were mixed in a Hobart blender for 20 minutes. The mixture was passed through a 40 mesh screen, dry granulated and then compressed to form tablets.

The so-formed sustained release tablet of the invention was found to undergo slow and relatively uniform release of the drug for up to a 16 hour period.

EXAMPLE 2

In a manner similar to that described in Example 1, except substituting enalapril for captopril, tablets containing 50 mg enalapril are prepared.

EXAMPLES 3 TO 5

Sustained release formulations capable of slowly releasing the antiarrhythmic agent procainamide hydrochloride for a period of up to 10 to 12 hours or more and having the following compositions are prepared as described in Example 1.

TABLE I

Formula Compositions
(Batch size 20 tablets)

| Example No. | Amount (gm) 3 | 4 | 5 |
|---|---|---|---|
| Composition | | | |
| Captopril HCl | 10 | 10 | 10 |
| Acrylic acid polymer cross-linked with polyallyl sucrose (Carbopol 934P) | 20 | 10 | 15 |
| Stearic acid | 0.6 | 0.4 | 0.5 |

EXAMPLE 6

A nadolol tablet in accordance with the present invention is prepared following the procedure of Example 1 except substituting 0.325 kg (40 mg per unit) nadolol for the captopril.

EXAMPLE 7

A propranolol tablet in accordance with the present invention is prepared following the procedure of Example 1 except substituting 0.325 kg (40 mg per unit) of propranolol for the captopril.

EXAMPLE 8

A fluphenazine HCl tablet in accordance with the present invention is prepared following the procedure of Example 1 except substituting 0.325 kg (10 mg per unit) of fluphenazine HCl for the captopril.

EXAMPLE 9

An aspirin tablet in accordance with the present invention is prepared following the procedure of Example 1 except substituting 0.325 kg (325 mg per unit) of aspirin for the captopril.

EXAMPLE 10

A theophylline tablet in accordance with the present invention is prepared following the procedure of Example 1 except substituting 0.325 kg (200 mg per unit) of theophylline for the captopril.

What is claimed is:

1. In a controlled release angiotensin converting enzyme inhibitor formulation in the form of an uncoated tablet from which upon ingestion angiotension converting enzyme inhibitor is released at a controlled rate, which tablet consists essentially of angiotensin converting enzyme inhibitor and from about 0.5 to about 5% by weight of a lubricant, the improvement which consists essentially of incorporating in said tablets from about 50 to about 80% by weight of an acrylic acid polymer or copolymer and from about 20 to about 65% by weight of angiotensin converting enzyme inhibitor.

2. The formulation as defined in claim 1 wherein the acrylic acid polymer or copolymer is a polymer of acrylic acid cross-linked with a polyfunctional agent.

3. The formulation as defined in claim 1 wherein the acrylic acid polymer or copolymer is a carboxyvinyl hydrophilic polymer of acrylic acid cross-linked with a polyalkenyl polyether.

4. The formulation as defined in claim 1 wherein the acrylic acid polymer or copolymer is polyacrylic acid, poly(hydroxyalkyl methacrylate), acrylic acid copolymer, or cross-linked hydrolyzed polyvinyl-ether maleic anhydride.

5. The formulation as defined in claim 1 wherein the weight of acrylic acid polymer or copolymer is at least 1.5 times the amount of the medicament.

6. The formulation as defined in claim 1 wherein the acrylic acid polymer or copolymer is acrylic acid polymer cross-linked with polyallyl sucrose.

7. The formulation as defined in claim 1 wherein the medicament is present in an amount within the range of from about 25 to about 35% by weight of the tablet.

8. The formulation as defined in claim 1 wherein the medicament is an angiotensin converting enzyme inhibitor.

9. The formulation as defined in claim 8 wherein the medicament is captopril.

10. The tablet as defined in claim 1 further including an auxiliary hydrocolloid which is methyl cellulose, hydroxypropyl cellulose, hydroxypropylmethyl cellulose, or a mixture of two or more of such hydrocolloids.

11. The tablet as defined in claim 1 further including a non-swellable binder and/or wax binder.

12. The tablet as defined in claim 10 wherein said wax binder is carnauba wax.

13. The tablet as defined in claim 10 wherein the non-swellable binder is lactose, gelatin, a starch, a sugar or gum acacia.

14. The tablet as defined in claim 1 wherein said lubricant is present in an amount within the range of from about 0.5 to about 8% by weight.

15. The tablet as defined in claim 14 wherein the lubricant is a magnesium stearate, stearic acid or a mixture thereof.

16. The tablet as defined in claim 1 wherein said medicament is captopril and said acrylic acid polymer or copolymer is acrylic acid polymer cross-linked with polyallyl sucrose.

* * * * *